United States Patent
Ci

(10) Patent No.: US 10,918,689 B2
(45) Date of Patent: Feb. 16, 2021

(54) SOLID BEVERAGE FOR CONDITIONING ALLERGIC CONSTITUTION AND METHOD FOR PRODUCING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 354 days.

(21) Appl. No.: 15/874,324

(22) Filed: Jan. 18, 2018

(65) Prior Publication Data

US 2019/0160130 A1 May 30, 2019

(30) Foreign Application Priority Data

Nov. 30, 2017 (CN) .......................... 2017 1 12401088

(51) Int. Cl.

| | | |
|---|---|---|
| *A61K 36/736* | (2006.01) | |
| *A61K 36/535* | (2006.01) | |
| *A61K 36/8967* | (2006.01) | |
| *A61K 36/185* | (2006.01) | |
| *A61K 36/8994* | (2006.01) | |
| *A61K 36/72* | (2006.01) | |
| *A61K 47/36* | (2006.01) | |
| *A61K 47/18* | (2017.01) | |
| *A61K 9/00* | (2006.01) | |
| *A23L 33/105* | (2016.01) | |
| *A23L 2/39* | (2006.01) | |
| *A23L 2/60* | (2006.01) | |
| *A61K 36/232* | (2006.01) | |
| *A61K 47/46* | (2006.01) | |
| *A61K 9/16* | (2006.01) | |
| *A61K 47/26* | (2006.01) | |
| *A23L 33/125* | (2016.01) | |

(52) U.S. Cl.
CPC .............. *A61K 36/736* (2013.01); *A23L 2/39* (2013.01); *A23L 2/60* (2013.01); *A23L 33/105* (2016.08); *A61K 9/0056* (2013.01); *A61K 9/0095* (2013.01); *A61K 9/1623* (2013.01); *A61K 9/1694* (2013.01); *A61K 36/185* (2013.01); *A61K 36/232* (2013.01); *A61K 36/535* (2013.01); *A61K 36/72* (2013.01); *A61K 36/8967* (2013.01); *A61K 36/8994* (2013.01); *A61K 47/18* (2013.01); *A61K 47/26* (2013.01); *A61K 47/36* (2013.01); *A61K 47/46* (2013.01); *A23L 33/125* (2016.08); *A23V 2002/00* (2013.01)

(58) Field of Classification Search
None
See application file for complete search history.

(56) References Cited

FOREIGN PATENT DOCUMENTS

| | | |
|---|---|---|
| CN | 104256616 A | 1/2015 |
| CN | 106509260 A | 3/2017 |
| CN | 107125391 A | 9/2017 |
| CN | 107184791 A | 9/2017 |
| CN | 107232470 A | 10/2017 |

OTHER PUBLICATIONS

CN105920085A translation (retrieved from Espacenet). (Year: 2016).*
https://m.haodf.com/touch/zhuanjiaguandian/1iangyonglings_991540423.htm; printed Sep. 9, 2020.

* cited by examiner

*Primary Examiner* — Michael Barker
(74) *Attorney, Agent, or Firm* — Cantor Colburn LLP

(57) ABSTRACT

The present application discloses a solid beverage for conditioning allergic constitution. The solid beverage comprises the following components in parts by weight: 18-45 parts of smoked plum, 10-30 parts of *perilla*, 18-45 parts of *lilium brownii*, 10-30 parts of purslane, 10-30 parts of *coix* seed, 10-30 parts of semen hoveniae, 7-20 parts of dahurian *angelica*, 15-40 parts of dextrin, 9-23 parts of maltodextrin, 9-23 parts of soluble starch and 0.1-0.3 parts of aspartame. The solid beverage of the present application is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, and has certain effects on the improvement of allergic constitution, and the production process thereof is suitable for industrial mass production.

10 Claims, 2 Drawing Sheets

SOLID BEVERAGE FOR CONDITIONING ALLERGIC CONSTITUTION AND METHOD FOR PRODUCING THE SAME

TECHNICAL FIELD

The present invention relates to the field of health foods, and particularly to a solid beverage for conditioning allergic constitution and a method for producing the same.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, yin deficiency constitution, qi deficiency constitution, phlegm-dampness constitution, damp-heat constitution, qi stagnation constitution, blood stasis constitution and allergic constitution, most of which are sub-healthy states.

Allergic constitution is a special body constitution resulting from the factors such as congenital deficiencies and endowment heredity, including congenital or hereditary physiological defects, congenital or hereditary diseases, allergic reactions, primary immunodeficiency and the like. The general characteristic of allergic constitution is congenital disorder, mainly characterized by physiological defects, allergic reactions and the like. People with allergic constitution generally have no other defects, but for people with abnormal native endowment, some may have malformations, and some may have physiological defects. The common manifestations are: people with allergic constitution usually suffer from asthma, wheal, throat itching, nasal obstruction, sneezing, etc.; people suffering from genetic diseases have the characteristics of vertical transmission, innateness, and being familial; and people with fetal-borne diseases have the characteristics of the mother's body affecting growth and development of fetus individuals and suffer from relevant diseases. People with allergic constitution have different psychological characteristics from each other, dependent on intrinsic nature. People with allergic constitution are susceptible to asthma, urticaria, pollinosis and drug allergies. People with allergic constitution are poor in adaptability to the external environment, for example, people with allergic constitution are poor in adaptability to the easy-to-sensitize season and are prone to chronic complaint.

Such sub-healthy constitution as allergic constitution belongs to chronic diseases and has a relatively long disease course, and requires a long-term medication and gradual conditioning, in order to achieve the effects of consolidating the vital essence and strengthening the origin, and strengthening the body resistance to eliminate pathogenic factors. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

Food is the best product for human beings to prevent diseases and keep healthy. The theory that "medicine and food share a common origin" is one of the most valuable contributions made by the original Chinese medicine to human beings. It is described in the *Rites of Zhou•Offices of the Heaven•Medicine* that "diseases are treated with the five flavors, the five grains and the five medicines", which demonstrates the physical health-care functions of food. The method of regulating body functions using the characteristics of food so as to obtain health or prevent or treat diseases is called dietary therapy. However, "therapy" is inferior to "nourishing", and food nourishing is an approach to increase resistance against diseases and enhance immunity by eating tonic food according to food nutrition in combination with the body conditions, so as to strengthen the body and prolong the life. It is described in *Prescriptions Worth a Thousand Gold* that "a physician should first know the cause of a disease to know why the disease is developed and treat the disease with food materials. Only when food materials are unable to treat the disease, can drugs be used." Thus, dietary therapy was not only the basic therapeutic approach of the physicians at that time, but also an important criterion for determining whether a physician was a great physician.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. Faced with the situations that there are various diseases in modern society, the age of onset becomes lower and lower and there are more and more sub-healthy people, dietary therapy gets more and more popular with the consumers due to its advantages of being healthy and natural, and with respect to the diseases that are easy to develop, it is of great significance to develop a food product that has the functions of life nourishing and health protection, has a good taste and conditions the allergic constitution, by using modern scientific technologies and methods and the theory that "medicine and food share a common origin", referring to the precious Chinese traditional life nourishing experience in combination with good accumulation of the traditional Chinese medicine on the aspect of conditioning allergic constitution.

DISCLOSURE OF THE INVENTION

The main object of the present invention is to provide a life nourishing and health protecting food product for conditioning allergic constitution.

In order to achieve the above object, according to one aspect of the present invention, there is provided a solid beverage for conditioning allergic constitution.

The solid beverage for conditioning allergic constitution according to the present invention comprises the following components in parts by weight: 18-45 parts of smoked plum, 10-30 parts of *perilla*, 18-45 parts of *lilium brownii*, 10-30 parts of purslane, 10-30 parts of *coix* seed, 10-30 parts of semen hoveniae, 7-20 parts of dahurian *angelica*, 15-40 parts of dextrin, 9-23 parts of maltodextrin, 9-23 parts of soluble starch and 0.1-0.3 parts of aspartame.

Further, the solid beverage for conditioning allergic constitution according to the present invention comprises the following components in parts by weight: 25-35 parts of smoked plum, 10-22 parts of *perilla*, 23-30 parts of *lilium brownii*, 18-30 parts of purslane, 13-25 parts of *coix* seed, 15-26 parts of semen hoveniae, 11-17 parts of dahurian *angelica*, 19-33 parts of dextrin, 13-18 parts of maltodextrin, 11-17 parts of soluble starch and 0.13-0.22 parts of aspartame.

Further, the solid beverage for conditioning allergic constitution according to the present invention comprises the following components in parts by weight: 30 parts of smoked plum, 20 parts of *perilla*, 30 parts of *lilium brownii*, 20 parts of purslane, 20 parts of *coix* seed, 20 parts of semen hoveniae, 12 parts of dahurian *angelica*, 27 parts of dextrin, 17 parts of maltodextrin, 17 parts of soluble starch and 0.14 parts of aspartame.

In order to achieve the above object, according to another aspect of the present invention, there is provided a method for producing a solid beverage for conditioning allergic constitution.

The method for producing a solid beverage for conditioning allergic constitution according to the present invention comprises the steps of:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

Further, the two-time decoction process in step (2) is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

Further, the temperature for the concentration in step (3) is 70-80° C., and the relative density of the prepared thick paste is 1.2-1.5 at the temperature of 50° C.

Further, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving;

(4.3) drying: putting the sieved particles prepared from step (4.2) into a boiling dryer for drying; and (4.4) secondary sieving: carrying out secondary sieving by using a wig-wag machine.

Further, the sieve for the primary sieving is a 12-mesh sieve, and the sieve for the secondary sieving is a 10-mesh sieve.

Further, in the drying process in step (4.3), the temperature of the materials is controlled to be 70-80° C., and the moisture of the final materials is controlled to be 5% or less.

Further, after the secondary sieving, the method further comprises a particle selecting step to select particles of 10-60 meshes.

The solid beverage of the present invention is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, and has certain effects on the improvement of allergic constitution, and the production process thereof is suitable for industrial mass production.

BRIEF DESCRIPTION OF DRAWINGS

The accompanying drawings, which constitute a part of the present application, are used to provide a further understanding of the present invention, so that other features, objects and advantages of the present application become more obvious. The illustrative drawings for embodiments of the present invention and the description thereof are used to explain the present invention, rather than constitute an improper limitation on the present invention. In the drawings.

DETAILED DESCRIPTION OF EMBODIMENTS

Figure 1:
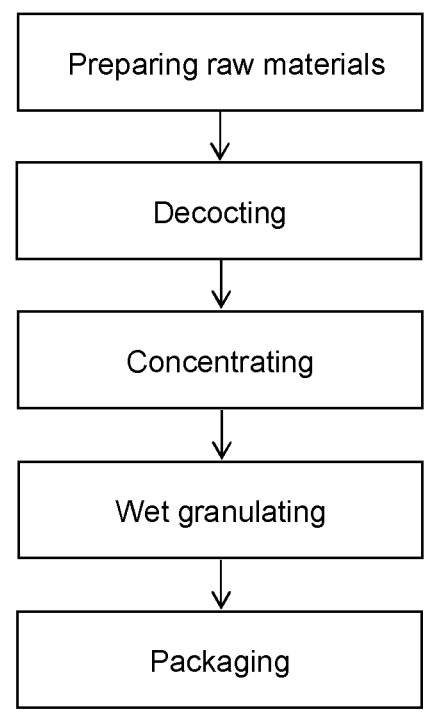
FIG. 1 is a production process of a solid beverage according to an embodiment of the present invention.

In order to enable a person skilled in the art to better understand the solutions of the present application, the technical solutions of the embodiments of the present invention will be described clearly and completely below with reference to the drawings of the embodiments of the present application. Apparently, the embodiments described are some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below with reference to the accompanying drawings and embodiments.

The main object of the present invention is to provide a life nourishing and health protecting food product for conditioning allergic constitution.

In order to achieve the above object, according to one aspect of the present invention, there is provided a solid beverage for conditioning allergic constitution.

The solid beverage for conditioning allergic constitution according to the present invention comprises the following components in parts by weight: 18-45 parts of smoked plum, 10-30 parts of *perilla*, 18-45 parts of *lilium brownii*, 10-30 parts of purslane, 10-30 parts of *coix* seed, 10-30 parts of semen hoveniae, 7-20 parts of dahurian *angelica*, 15-40 parts of dextrin, 9-23 parts of maltodextrin, 9-23 parts of soluble starch and 0.1-0.3 parts of aspartame.

Smoked plum is sour and astringent in flavor and neutral in nature; acts on liver, spleen, lung and large intestine; has the efficacies of astringing the lung, astringing the intestines, promoting the secretion of saliva or body fluid, and calming *ascaris*; and is used for chronic cough caused by lung deficiency, prolonged diarrhea and dysentery, deficiency-heat consumptive thirst, *ascaris*-caused syncope, vomiting and abdominal pain.

*Perilla* is acrid in flavor and warm in nature; acts on lung and spleen; has the efficacies of relieving exterior syndromes and dispelling pathogenic cold, and relieving qi stagnancy in stomach; and is used for common cold due to wind-cold, cough and nausea, vomiting of pregnancy and poisoning from fish and crabs.

*Lilium brownii* is sweet in flavor and slightly cold in nature; acts on lung and heart; has the efficacies of moistening lung for arresting cough, clearing away the heart fire and tranquilizing; and is used for cough caused by dryness-heat, over-strained cough, hemoptysis, dysphoria, pavor, insomnia and dreamful sleep.

Purslane is sour in flavor and cold in nature; acts on liver and large intestine; has the efficacies of clearing away heat and toxic materials, cooling blood for hemostasis, and relieving dysentery; and is used for heat-toxicity and bloody dysentery, abscess and furuncle, eczema, erysipelas, snake and insect bites, hematochezia, hemorrhoidal bleeding, metrorrhagia and hematochezia.

*Coix* seed is sweet and light in flavor and slightly cold and non-toxic in nature; acts on spleen, stomach, lung and large intestine; has the efficacies of clearing heat and promoting diuresis, eliminating wind-damp, diuresis, nourishing lung, apocenosis, strengthening the spleen and stomach, strengthening muscles and bones; and is used for rheumatism and pantalgia, dampness-heat beriberi, dampness-heat muscular constriction, arthralgia due to dampness, edema, pulmonary collapse and pulmonary abscess, coughing and spitting pus and blood, throat impediment and abscess, intestinal carbuncle and heat stranguria.

Semen hoveniae is sweet in flavor and neutral in nature; acts on stomach; has the efficacies of relieving alcoholism, quenching thirst and relieving restlessness, preventing or arresting vomiting, and promoting urination and defecation; and is used for intoxication, polydipsia, vomiting, and difficulty in urination and defecation.

Dahurian *angelica* is acrid in flavor and warm in nature; acts on lung, spleen, stomach; has the efficacies of relieving exterior syndromes and dispelling pathogenic cold, dispelling wind and relieving pain, relieving stuffy nose, eliminating dampness and checking vaginal discharge, apocatastasis and apocenosis, and dispelling wind and arresting itching; and is used for common cold due to wind-cold, headache, toothache, arthralgia due to wind-dampness, nasosinusitis, morbid leukorrhea, and pyogenic infection with abscess.

Allergic constitution such as allergies is mainly inherited from parents, is incurred by epidemic pathogenic factor, has the manifestations of erythra, allergic rhinitis, or infertility. According to the constitution characteristics thereof, it is caused by qi-deficiency induced superficies unconsolidation, blood heat's facilitating onset of diseases caused by pathogenic wind, and inability of genetic endowment to endure epidemic pathogenic factor. The treatment therefor takes the general principle of invigorating qi for consolidating superficies, cooling blood and calming endogenous wind, and conditioning body. If superficial qi is consolidated, the body can resist pathogenic factors, and if blood and qi function normally, pathogenic wind is calmed. In this prescription, smoked plum astringes vital essence, *lilium brownii* nourishes yin and clears heat, *perilla* relieves epigastric distention and consolidates superficies, and they jointly serve the function of invigorating qi for consolidating superficies. Purslane has the effect of resisting allergies; dahurian *angelica* frees the nasal orifices; semen hoveniae can relieve alcoholism and resist allergies; and *coix* seed invigorates spleen to remove dampness, and can enhance the body immunity. In the present invention, smoked plum, *lilium brownii* and *perilla* are dominant (monarch) components, purslane, dahurian *angelica* and semen hoveniae are subordinate (ministerial) components, and *coix* seed is an adjuvant (envoy) component. In addition, dextrin, maltodextrin and aspartame, on the one hand, can give play to medicinal effect and balance the nutritional ingredients, and on the other hand, can be used for flavoring.

As shown in FIG. 1, the method for producing a solid beverage for conditioning allergic constitution comprises the steps of:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use, wherein the proportion of each raw material provided in the present invention is used herein;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste;

(4) wet granulation: mixing and stirring dextrin, maltodextrin, soluble starch and aspartame to obtain a mixture adjuvant, adding the thick paste prepared in step (3) to the mixture adjuvant, and stirring the same for granulation; and (5) packaging: subjecting the product resulting from the wet granulation to the packaging step to obtain a finished product.

The purpose of step (1) is to remove fat from the seed medicinal materials, pulverize the resultant seed medicinal materials and pass them through a 2-mesh sieve; the rhizomatic medicinal materials contain cellulose, and are rich in starch, and cutting or pulverization extraction can effectively retain the target ingredients thereof, and prevent polysaccharide swelling; and cleansing can remove impurities and soil, and effectively reduce the residuals of pollutants such as heavy metals and pesticides.

The two-time decoction process in step (2) is carried out as follows: the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

The temperature for the concentration in step (3) is 70-80° C., and the relative density of the prepared thick paste is 1.2-1.5 at the temperature of 50° C. The low-temperature evaporation can effectively reduce the decomposition of thermosensitive components, such as citric acid, malic acid, oxalic acid and other organic acids, and leads to high concentration efficiency without discharge of solvent steam, which facilitates evaporation, and is pollution-free to the environment, as it is carried out in an airtight space.

Figure 2:
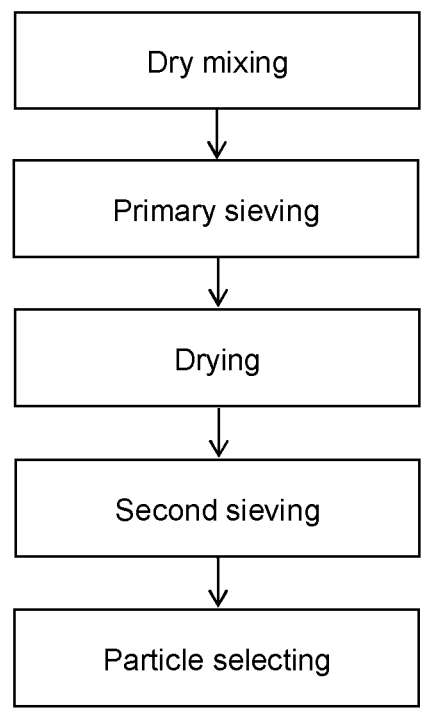
FIG. 2 is the specific steps of wet granulation in the production process of the solid beverage according to an embodiment of the present invention.

As shown in FIG. 2, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant, wherein the proportion of each raw material provided in the present invention is used herein;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving, wherein stirring granulation can preferably prevent separation of the components, and since segregation phenomenon can easily occur due to the existence of differences in the particle size and density of the mixed extract components, granulation not only can effectively solve this problem, but also can remarkably improve the solubility;

(4.3) drying: putting the sieved particles prepared from step (4.2) into a boiling dryer for drying, wherein fluidized drying can effectively control the particle size distribution and control the product moisture; and (4.4) secondary sieving: carrying out secondary sieving by using a wig-wag machine, wherein by means of the secondary sieving, it is possible to control the particle distribution, bulk density and compactness.

In the above steps, the sieve for the primary sieving is a 12-mesh sieve, and the sieve for the secondary sieving is a 10-mesh sieve.

In the drying process in the above step (4.3), the temperature of the materials is controlled to be 70-80° C., and the moisture of the final materials is controlled to be 5% or less. In this step, pot turning can be frequently carried out according to the drying condition of the materials, so that the final material moisture meets the requirements.

On the basis of the implementation modes above, after the secondary sieving, the method further comprises a particle selecting step to select particles of 10-60 meshes. By means of particle selection, it is possible to improve the appearance and uniformity of the product particles. In practice, after the completion of the particle selection, it is feasible to make a record and tag the product to indicate the product name, the lot number, the specification, the net weight, the production date, the post name and the responsible person, fill in the equipment receipt, and transfer the product into an intermediate station.

The production method thereof is as follows:

(1) preparation of raw materials: subjecting smoked plum, perilla, lilium brownii, purslane, coix seed, semen hoveniae and dahurian angelica to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 70° C., and the relative density of the prepared thick paste is 1.2 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 70° C., and the moisture of the final materials is controlled to be 5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 1

The solid beverage for conditioning allergic constitution comprises the following components in parts by weight: 18 parts of smoked plum, 10 parts of perilla, 18 parts of lilium brownii, 10 parts of purslane, 10 parts of coix seed, 10 parts of semen hoveniae, 7 parts of dahurian angelica, 15 parts of dextrin, 9 parts of maltodextrin, 9 parts of soluble starch and 0.1 parts of aspartame.

Embodiment 2

The solid beverage for conditioning allergic constitution comprises the following components in parts by weight: 45 parts of smoked plum, 30 parts of perilla, 45 parts of lilium brownii, 30 parts of purslane, 30 parts of coix seed, 30 parts of semen hoveniae, 20 parts of dahurian angelica, 40 parts of dextrin, 23 parts of maltodextrin, 23 parts of soluble starch and 0.3 parts of aspartame.

The production method thereof is as follows:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 80° C., and the relative density of the prepared thick paste is 1.5 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 80° C., and the moisture of the final materials is controlled to be 3%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 3

The solid beverage for conditioning allergic constitution comprises the following components in parts by weight: 25 parts of smoked plum, 10 parts of *perilla,* 23 parts of *lilium brownii,* 18 parts of purslane, 13 parts of *coix* seed, 15 parts of semen hoveniae, 11 parts of dahurian *angelica,* 19 parts of dextrin, 13 parts of maltodextrin, 11 parts of soluble starch and 0.13 parts of aspartame.

The production method thereof is as follows:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 75° C., and the relative density of the prepared thick paste is 1.45 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 78° C., and the moisture of the final materials is controlled to be 3.4%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 4

The solid beverage for conditioning allergic constitution comprises the following components in parts by weight: 35 parts of smoked plum, 22 parts of *perilla,* 30 parts of *lilium brownii,* 30 parts of purslane, 25 parts of *coix* seed, 26 parts of semen hoveniae, 17 parts of dahurian *angelica,* 33 parts of dextrin, 18 parts of maltodextrin, 17 parts of soluble starch and 0.22 parts of aspartame.

The production method thereof is as follows:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 73° C., and the relative density of the prepared thick paste is 1.33 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 72° C., and the moisture of the final materials is controlled to be 4.5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 5

The solid beverage for conditioning allergic constitution comprises the following components in parts by weight: 30 parts of smoked plum, 20 parts of *perilla,* 30 parts of *lilium brownii,* 20 parts of purslane, 20 parts of *coix* seed, 20 parts of semen hoveniae, 12 parts of dahurian *angelica,* 27 parts of dextrin, 17 parts of maltodextrin, 17 parts of soluble starch and 0.14 parts of aspartame.

The production method thereof is as follows:

(1) preparation of raw materials: subjecting smoked plum, *perilla, lilium brownii*, purslane, *coix* seed, semen hoveniae and dahurian *angelica* to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 77° C., and the relative density of the prepared thick paste is 1.4 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 76° C., and the moisture of the final materials is controlled to be 3.8%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Experimental Example 1

The following is a test for the effects of the solid beverage for conditioning allergic constitution, which is prepared according to embodiment 5 of the present invention.

The basic conditions of the cases: 100 clinical cases of allergic constitution, including 50 male cases and 50 female cases. The youngest was aged 9, and the oldest was aged 72. 10 cases had allergic constitution, and often had nasal obstruction, sneezed, had a runny nose, even when they did not have a cold, and were susceptible to asthma; 15 cases easily got allergic to drugs and food; 10 cases were susceptible to smell and pollen allergies; 10 cases were prone to seasonal allergies; 25 cases were susceptible to skin urticaria, often had magenta spots and ecchymoses on the skin due to allergies, and once scratched, the skin often turned red with scratches; and 30 cases had other symptoms of allergic constitution.

The usage and dosage: the solid beverage was administered 8 g each time, twice a day; and was administered after being brewed with boiling water.

The evaluation criteria for therapeutic effects:

Being cured: the clinical symptoms were completely eliminated, and normal life was restored.

Being effective: the clinical symptoms were partially eliminated, and various signs were gradually improved.

Being ineffective: the symptoms and signs were not obviously improved.

Result statistics: 53 cases were cured, the solid beverage was effective to 38 cases and ineffective to 9 cases, i.e., the solid beverage was effective to 91 cases in total, therefore the total effective rate was 91%.

Typical Cases:

Patient 1, Ms. Huang, female, 27 years old. Ms. Huang saw a doctor on Mar. 22, 2016. At that time, she often had abdominal pain, diarrhea, vomiting, or unbearably skin itching after eating food such as fish, shrimps and crabs. The physical constitution in this case was considered as allergic constitution, and the solid beverage prepared in embodiment 1 was administered after being brewed with boiling water, once a day for one month. The symptoms disappeared after one month of administration.

Patient 2, Mr. Ma, male, 30 years old. Mr. Ma saw a doctor on Apr. 18, 2015. At that time, he usually had a cough, which was a dry cough without phlegm and was paroxysmal when the season changed or when he smelt unusual odors, often sneezed, and was easy to have allergic response and have skin itching in spring. He once had eczema and urticaria. The physical constitution in this case was considered as allergic constitution, and the formulation in embodiment 2 was administered after being brewed with boiling water, once a day for two months. The symptoms disappeared after two months of administration, and have not relapsed so far.

Patient 3, Ms. Peng, female, 15 years old. Ms. Peng saw a doctor on May 26, 2016. She was easily allergic to pollen at that time, and had the manifestations of diarrhea and appearance of red spots and ecchymoses on the face or body. The physical constitution in this case was considered as allergic constitution, and the formulation in embodiment 3 was administered after being brewed with boiling water, once a day for half a month. The symptoms disappeared after half a month of administration.

Patient 4, Mr. Mou, male, 66 years old. Mr. Mou saw a doctor on Apr. 18, 2016. At that time, he often had nasal obstruction, sneezed, had a runny nose, even when he did not have a cold, and would easily develop asthma, and these symptoms became serious when season changed. The physical constitution in this case was considered as allergic constitution, and the formulation in embodiment 4 was administered, once a day for one month. The symptoms disappeared after one month of administration, and have not relapsed so far.

Experimental Example 2: Sensory Evaluation

The solid beverages prepared in embodiments 1-5 were brewed with boiling water and used as experimental groups, and the mixed liquid medicine after two decoctions prepared in the process step (2) in embodiment 5 was used a control group, three replicates of samples were collected from each of the experimental groups and the control group, and were subjected to sensory evaluation by 20 professional sensory assessors. The sensory evaluation scoring criteria are shown in table 1, and the sensory evaluation results are shown in table 2.

TABLE 1

Sensory Evaluation Scoring Criteria

| items | sensory evaluation | score |
|---|---|---|
| color | relatively dark | 1 |
| | intermediate | 5 |
| | relatively light | 1 |
| smell | strong smell of traditional Chinese medicine | 1 |
| | light smell of traditional Chinese medicine | 3 |
| | medicine fragrance | 5 |
| | relatively light | 3 |
| | light | 1 |
| taste | bitter and astringent | 1 |
| | relatively bitter | 3 |
| | fragrant and sweet | 5 |
| | relatively sweet | 3 |
| | excessively sweet | 1 |
| fineness and smoothness | fine and smooth | 5 |
| | having granular sensation | 3 |
| | having a throat-scratching feeling | 1 |
| | being hard to swallow | 0 |
| overall evaluation | poor | — |
| | ordinary | — |
| | good | — |

TABLE 2

Sensory Evaluation Results of Solid Beverages

| | items | control group | embodiment 1 | embodiment 2 | embodiment 3 | embodiment 4 | embodiment 5 | average |
|---|---|---|---|---|---|---|---|---|
| sensory evaluation (marks) | color | 43 | 93 | 96 | 92 | 95 | 97 | 94.6 |
| | smell | 24 | 95 | 95 | 97 | 97 | 94 | 95.6 |
| | taste | 58 | 90 | 97 | 95 | 96 | 96 | 94.8 |
| | fineness and smoothness | 88 | 91 | 93 | 92 | 92 | 93 | 92.2 |
| | average | 53.25 | 92.25 | 95.25 | 94 | 95 | 95 | |
| overall evaluative (person-time) | good | 5 | 18 | 20 | 19 | 19 | 20 | 19.2 |
| | ordinary | 6 | 2 | 0 | 1 | 1 | 0 | 0.8 |
| | poor | 9 | 0 | 0 | 0 | 0 | 0 | 0 |

As can be known from the above experimental results, the average scores on the aspects of color, smell, taste and fineness and smoothness of the solid beverages prepared in embodiments 1 to 5 as given by the 20 professional sensory assessors are all higher than the corresponding scores given for the control group. The results show that the solid beverage provided by the present invention is greatly improved in smell and taste, as compared with the liquid medicine obtained by decocting the traditional Chinese medicine decoction pieces, moreover, sweet flavor has been added thereto, the taste and the fine and smooth feeling are greatly improved, which makes the solid beverage provided by the present invention very suitable for everyday drinking.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A solid beverage, comprising the following components in parts by weight: 18-45 parts of smoked plum, 10-30 parts of *perilla*, 18-45 parts of *lilium brownii*, 10-30 parts of purslane, 10-30 parts of *coix* seed, 10-30 parts of semen hoveniae, 7-20 parts of dahurian *angelica*, 15-40 parts of dextrin, 9-23 parts of maltodextrin, 9-23 parts of soluble starch and 0.1-0.3 parts of aspartame.

2. The solid beverage according to claim 1, characterized by comprising the following components in parts by weight: 25-35 parts of smoked plum, 10-22 parts of *perilla*, 23-30 parts of *lilium brownii*, 18-30 parts of purslane, 13-25 parts of *coix* seed, 15-26 parts of semen hoveniae, 11-17 parts of dahurian *angelica*, 19-33 parts of dextrin, 13-18 parts of maltodextrin, 11-17 parts of soluble starch and 0.13-0.22 parts of aspartame.

3. The solid beverage according to claim 1, characterized by comprising the following components in parts by weight: 30 parts of smoked plum, 20 parts of *perilla*, 30 parts of *lilium brownii*, 20 parts of purslane, 20 parts of *coix* seed, 20 parts of semen hoveniae, 12 parts of dahurian *angelica*, 27 parts of dextrin, 17 parts of maltodextrin, 17 parts of soluble starch and 0.14 parts of aspartame.

4. A method for producing a solid beverage comprising the steps of:
   (1) preparation of raw materials: taking subjecting smoked plum, *perilla, lilium brownii*, purslane, *coix* seed, semen hoveniae and dahurian *angelica* for cleansing, cutting and pulverization, and then mixing them for later use;
   (2) decoction: decocting the mixture resulting from step (1) with water twice to obtain a liquid;
   (3) concentration: pumping the liquid prepared in step (2) into an inspissator through a pipe to concentrate the same into thick paste; and
   (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

5. The method for producing a solid beverage according to claim 4, characterized in that, the decocting the mixture resulting from step (1) with water twice to obtain a liquid in step (2) is carried out by the following processes of:
   (a): adding water that is 10 times the weight of the mixture prepared in step (1), heating and boiling the resultant mixture, and pumping the liquid into a stainless-steel liquid storage tank through a pipeline filter immediately after boiling for 1.5 hours (starting from boiling); and
   (b): adding water that is 8 times the weight of the mixture prepared in step (1), heating and boiling the resultant mixture, and pumping the liquid into the stainless-steel liquid medicine storage tank through the pipeline filter immediately after boiling for 1.5 hours (starting from boiling) to evenly mix the liquid with the liquid obtained from the process (a).

6. The method for producing a solid beverage according to claim 4, characterized in that, the temperature for the concentration in step (3) is 70-80° C., and the relative density of the prepared thick paste is 1.2-1.5 at the temperature of 50° C.

7. The method for producing a solid beverage according to claim 4, characterized in that, the wet granulation in step (4) comprises the steps of:
   (4.1) dry mixing: putting dextrin, maltodextrin, soluble starch and aspartame into an mixer-granulator for mixing and stirring for 15 minutes to obtain a mixture adjuvant;
   (4.2) primary sieving: adding batchwise the thick paste extracted from step (3) to the mixture adjuvant for mixing, stirring and granulation in the mixer-granulator to obtain a soft material which is then subjected to primary sieving;
   (4.3) drying: putting the sieved particles prepared from step (4.2) into a boiling dryer for drying; and
   (4.4) secondary sieving: carrying out secondary sieving by using an oscillating granulator.

8. The method for producing a solid beverage according to claim 7, characterized in that, the sieve for the primary sieving is a 12-mesh sieve, and the sieve for the secondary sieving is a 10-mesh sieve.

9. The method for producing a solid beverage according to claim 7, characterized in that, in the drying process in step (4.3), the temperature of the materials is controlled to be 70-80° C., and the moisture of the final materials is controlled to be 5% or less.

10. The method for producing a solid beverage according to claim 7, characterized in that, after the secondary sieving, the method further comprises a particle selecting step to select particles of 10-60 meshes.

* * * * *